| (12) United States Patent | (10) Patent No.: US 8,267,862 B2 |
|---|---|
| Jeong et al. | (45) Date of Patent: Sep. 18, 2012 |

(54) APPARATUS AND METHOD FOR MONITORING HEALTH INDEX USING ELECTROCONDUCTIVE FIBER

(75) Inventors: Ji Wook Jeong, Daejeon (KR); Yong Won Jang, Daejeon (KR); Seung Hwan Kim, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 324 days.

(21) Appl. No.: 12/474,520

(22) Filed: May 29, 2009

(65) Prior Publication Data

US 2010/0160743 A1 Jun. 24, 2010

(30) Foreign Application Priority Data

Dec. 18, 2008 (KR) .................. 10-2008-0129160

(51) Int. Cl.
*A61B 5/00* (2006.01)
*A61B 5/08* (2006.01)
(52) U.S. Cl. ......... 600/300; 600/527; 600/534; 600/595
(58) Field of Classification Search .................. 600/382, 600/384, 386
See application file for complete search history.

(56) References Cited

U.S. PATENT DOCUMENTS

| 5,207,230 A * | 5/1993 | Bowers .................. 600/593 |
| 7,052,469 B2 | 5/2006 | Minamiura et al. |
| 2004/0225227 A1 * | 11/2004 | Newman .................. 600/534 |
| 2005/0062486 A1 * | 3/2005 | Qi et al. .................. 324/693 |
| 2006/0155175 A1 * | 7/2006 | Ogino et al. .................. 600/301 |
| 2007/0016098 A1 * | 1/2007 | Kim et al. .................. 600/546 |
| 2007/0038057 A1 | 2/2007 | Nam et al. |
| 2007/0060802 A1 | 3/2007 | Ghevondian et al. |
| 2007/0293781 A1 * | 12/2007 | Sims et al. .................. 600/534 |
| 2010/0160763 A1 | 6/2010 | Tsai et al. |
| 2010/0286546 A1 * | 11/2010 | Tobola et al. .................. 600/534 |
| 2010/0317954 A1 | 12/2010 | Jeong et al. |

FOREIGN PATENT DOCUMENTS

| JP | 2006-115931 A | 5/2006 |
| JP | 3-150673 U | 4/2009 |
| KR | 1020040045364 A | 6/2004 |
| KR | 1020060005094 A | 1/2006 |
| KR | 1020070060971 A | 6/2007 |
| KR | 10-0819050 B1 | 3/2008 |
| KR | 1020080073531 A | 8/2008 |

* cited by examiner

*Primary Examiner* — Henry M. Johnson, III
*Assistant Examiner* — Davin K Sands
(74) *Attorney, Agent, or Firm* — Ladas & Parry LLP (57) ABSTRACT

Provided are an apparatus and method for monitoring a health index using an electroconductive fiber. In the apparatus, a bio signal acquiring unit measures a bio signal using an electroconductive fiber which is worn around a part of a user's body and in which a resistance is varied according to a user's body volume or body temperature. A health index acquiring unit analyzes the bio signal to acquire a health index. A health index notifying unit notifies the health index. Accordingly, the health index can be easily monitored without limitations on the user's behavior.

19 Claims, 8 Drawing Sheets

APPARATUS AND METHOD FOR MONITORING HEALTH INDEX USING ELECTROCONDUCTIVE FIBER

CROSS-REFERENCE TO RELATED APPLICATIONS

This application claims the priority of Korean Patent Application No. 2008-0129160 filed on Dec. 18, 2008, in the Korean Intellectual Property Office, the disclosure of which is incorporated herein by reference.

BACKGROUND OF THE INVENTION

1. Field of the Invention

The present application relates to an apparatus for monitoring health index, and more particularly, to an apparatus and method for monitoring health index using an electroconductive fiber, which is implemented in a wearable type, so that a health index can be monitored without limitations on the user's behavior.

2. Description of the Related Art

As medical technology has advanced and the quality of user's lives has improved, personal attention to health care is gradually growing. Accordingly, various kinds of medical instruments, capable of monitoring a health index, have been developed and are widely used in private homes and in medical facilities such as hospitals and medical centers.

However, existing medical instruments have disadvantages in that exact diagnostic results can be acquired only when a user takes a certain posture at a certain place. That is, a user's behavior is limited when monitoring a health index through existing medical instruments.

Therefore, for the convenience of user in need of medical monitoring, there is a growing need to monitor a health index while minimizing limitations on the user's behavior.

Meanwhile, electroconductive fibers have been developed which integrate fiber technology with electronic technology. Those electroconductive fibers have electrical properties, which vary according to external environment.

When electroconductive fibers are used in clothes, for example, the clothes themselves can have various electronic functions.

The electroconductive fibers of the present application are electroconductive fibers having electrical properties such that their resistances are varied according to variations in their lengths.

SUMMARY OF THE INVENTION

An aspect of the present application provides an apparatus and method for monitoring a health index using an electroconductive fiber whose resistance is varied according to a user's body volume or body temperature, which are capable of monitoring a health index without limitations on the user's behavior.

According to an aspect of the present invention, there is provided an apparatus for monitoring a health index using an electroconductive fiber, including: a bio signal acquiring unit measuring a bio signal using an electroconductive fiber which is worn around a part of a user's body and of which resistance is varied according to a user's body volume or body temperature; a health index acquiring unit analyzing the bio signal to acquire a health index; and a health index notifying unit notifying the health index.

The bio signal may contain information about one or more of pulse frequency, electrocardiogram, respiration rate, and body temperature.

When the electroconductive fiber is worn around a wrist, the bio signal may contain information about the pulse frequency; when the electroconductive fiber is worn around a chest where a heart is located, the bio signal may contain information about the electrocardiogram; when the electroconductive fiber is worn around an abdomen between a solar plexus where a diaphragm is located and a navel, the bio signal may contain information about the electrocardiogram; and when the electroconductive fiber is worn around an abdomen or an armpit that is least affected by an exterior temperature, the bio signal may contain information about the body temperature.

The electroconductive fiber may be implemented in a band type to surround a part of the user's body or in a garment type woven together with cloth. In this case, the electroconductive fiber may be arranged in a spiral shape.

The electroconductive fiber may be implemented in an attachment type that is attachable to cloth. In this case, the electroconductive fiber may be arranged in a zigzag shape.

The bio signal acquiring unit may include: a signal detecting unit outputting an analog signal having a voltage corresponding to the resistance of the electroconductive fiber; a bio signal converting unit converting the analog signal into a digital bio signal; and a bio signal transmitting unit transmitting the digital bio signal to the health index acquiring unit.

The signal detecting unit may include: a voltage provider generating a voltage necessary for detection of the bio signal; and a voltage division circuit dividing the voltage according to the resistance of the electroconductive fiber and generating an analog signal having a voltage corresponding to the resistance of the electroconductive fiber.

The bio signal acquiring unit may further include a bio signal displaying unit outputting the bio signal in image and/or sound form.

The health index acquiring unit may include: a bio signal receiving unit receiving the bio signal transmitted from the bio signal acquiring unit; a health index generating unit analyzing the bio signal to acquire the health index; and a health index outputting unit outputting the health index to the health index notifying unit.

The health index generating unit may generate the health index by analyzing the bio signal according to a bio signal analysis standard previously defined by kinds of the health index.

The health index notifying unit may include: an image outputting unit outputting an image corresponding to the health index; a sound outputting unit outputting a sound corresponding to the health index; and a communication unit connecting to a server located in an external network to provide the health index to the server.

The bio signal acquiring unit, the health index acquiring unit, and the health index notifying unit may perform a communication, based on one of a cable communication, a wireless communication, and an infrared communication.

According to another aspect of the present invention, there is provided a method for monitoring a health index using an electroconductive fiber, including: measuring a bio signal using an electroconductive fiber which is worn around a part of a user's body and in which a resistance is varied according to a user's body volume or body temperature; analyzing the bio signal to acquire a health index; and notifying the health index to the user.

The bio signal may contain information about one or more of pulse frequency, electrocardiogram, respiration rate, and body temperature.

BRIEF DESCRIPTION OF THE DRAWINGS

The above and other aspects, features and other advantages of the present application will be more clearly understood from the following detailed description taken in conjunction with the accompanying drawings, in which.

DETAILED DESCRIPTION OF THE PREFERRED EMBODIMENT

Exemplary embodiments of the present application will now be described in detail with reference to the accompanying drawings.

Hereinafter, preferred embodiments of the present application will be described in detail with reference to the accompanying drawing in such a manner that the present application may easily be carried out by a person with ordinary skill in the art to which the present application pertains. In the following explanation about the operational principles related to the preferred embodiments of the present invention, detailed descriptions related to well-known functions or configurations will be ruled out in order not to unnecessarily obscure subject matters of the present invention.

In the drawings, parts having no relation to the description are omitted for clarity, and like reference numerals are used to refer to like elements throughout the specification.

Moreover, when it is described that one part comprises (or includes or has) certain elements, it should be understood that it may further comprise (or include or have) other elements if there is no specific limitation.

Figure 1:
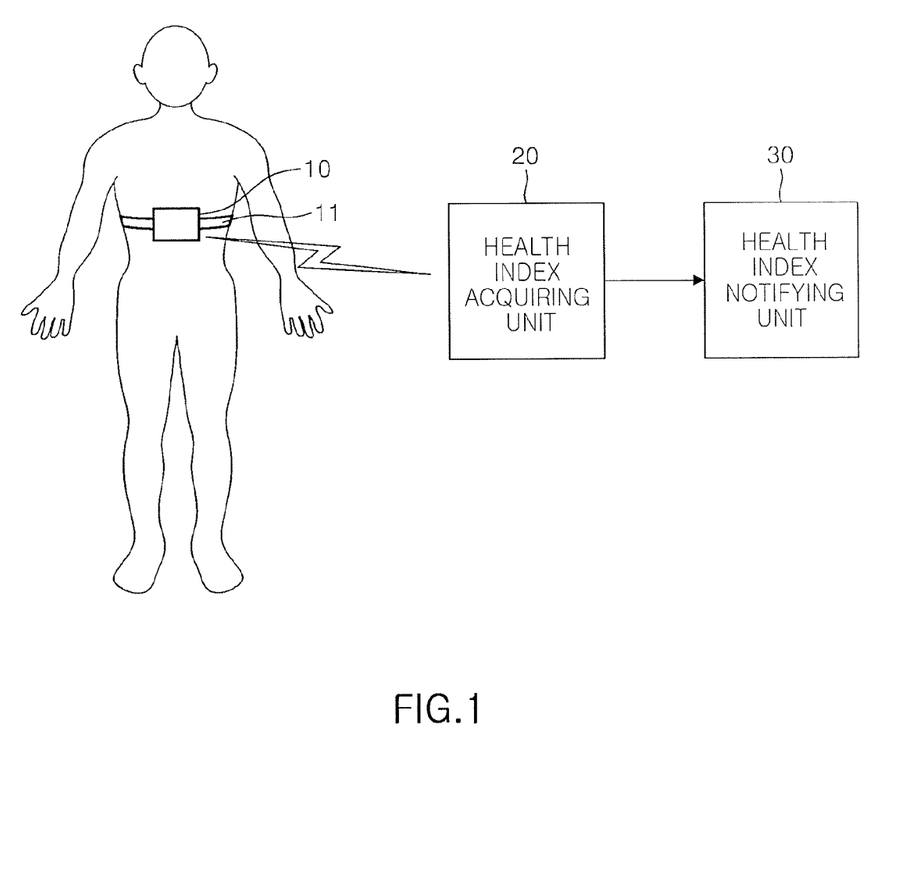
FIG. 1 is a conceptual diagram of an apparatus for monitoring a health index using an electroconductive fiber according to an embodiment of the present invention.

FIG. 1 is a conceptual diagram of an apparatus for monitoring a health index using an electroconductive fiber according to an embodiment of the present invention.

Referring to FIG. 1, the apparatus for monitoring a health index using an electroconductive fiber according to an embodiment of the present application includes a bio signal acquiring unit 10, a health index acquiring unit 20, and a health index notifying unit 30. The bio signal acquiring unit 10 measures a bio signal using an electroconductive fiber 11 worn around a user's body. The health index acquiring unit 20 acquires a health index through analysis of the bio signal. The health index notifying unit 30 notifies a user of the health index in image or sound form, or provides the health index to a server located in an external network.

As the user's body volume or body temperature changes, the length of the electroconductive fiber 11 of FIG. 1 is varied and thus its resistance is varied.

After a user wears the electroconductive fiber 11 around his body, a bio signal containing information such as pulse frequency, electrocardiogram, respiration rate or body temperature is acquired using the electrical properties of the electroconductive fiber 11 whose resistance is varied according to the external environment.

The kinds of information that can be acquired using the electroconductive fiber 11 are determined according to the wearing positions of the electroconductive fiber 11. For example, a bio signal containing information about pulse frequency can be acquired through an electroconductive fiber 11 worn around a wrist; a bio signal containing information about an electrocardiogram can be acquired through an electroconductive fiber 11 worn around a chest closest to a heart; a bio signal containing information about respiration rate can be acquired through an electroconductive fiber 11 worn around an abdomen close to a diaphragm; and a bio signal containing information about a body temperature can be acquired through an electroconductive fiber 11 worn around the abdomen or an armpit (axilla) that is least affected by exterior temperature.

That is, by wearing the electroconductive fiber 11 around the part of the body where the pulse frequency, the electrocardiogram, the respiration rate and the body temperature are most efficiently measured anatomically, various bio signals can be acquired without limitations on a user's behavior.

Figure 2A:
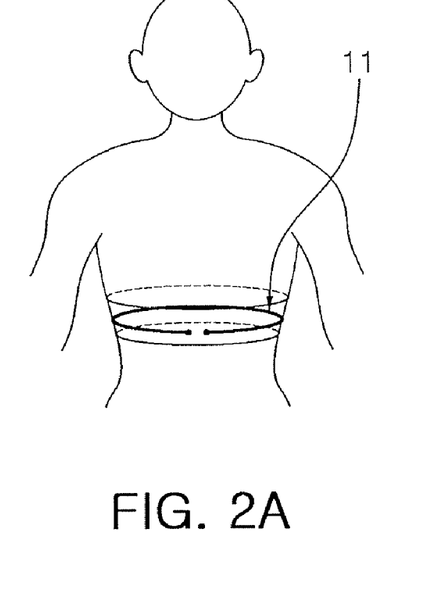
FIG. 2A illustrates an implementation example of the electroconductive fiber according to an embodiment of the present invention.
Figure 2B:
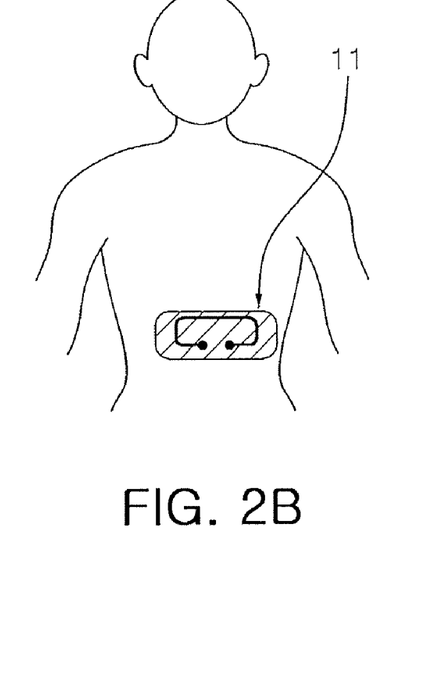
FIG. 2B illustrates another implementation example of the electroconductive fiber according to an embodiment of the present invention.
Figure 2C:
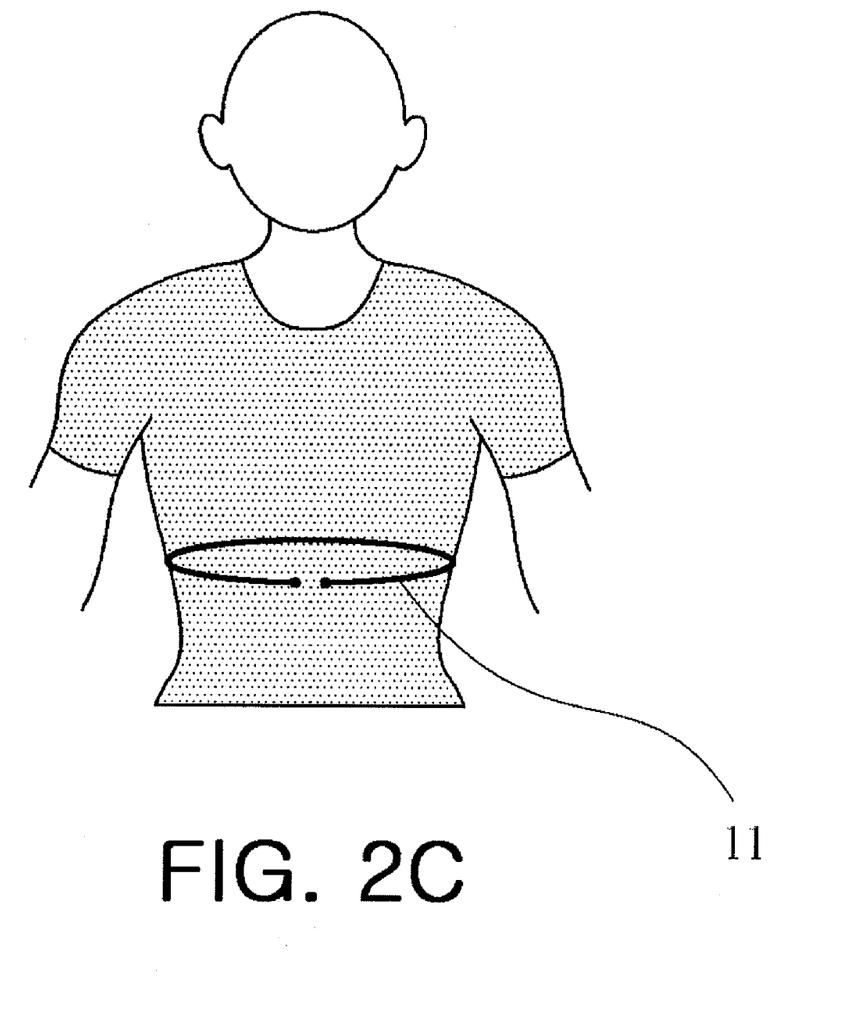
FIG. 2C illustrates still another implementation example of the electroconductive fiber according to an embodiment of the present invention.
Figure 3A:
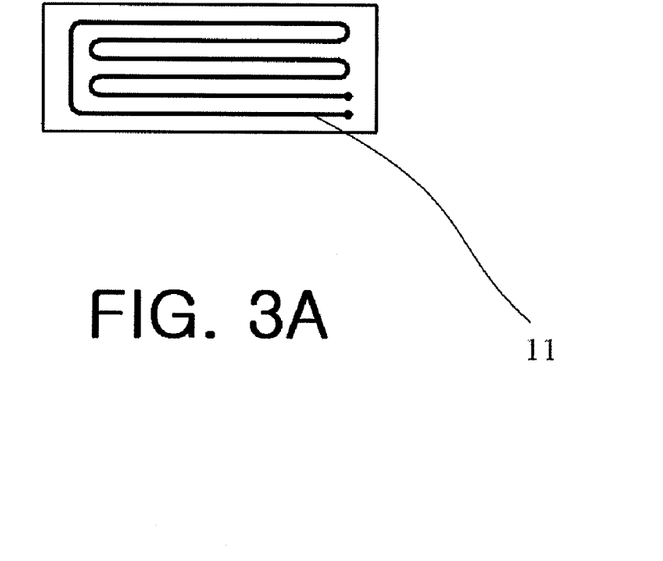
FIG. 3A illustrates an arrangement example of the electroconductive fiber according to an embodiment of the present invention.
Figure 3B:
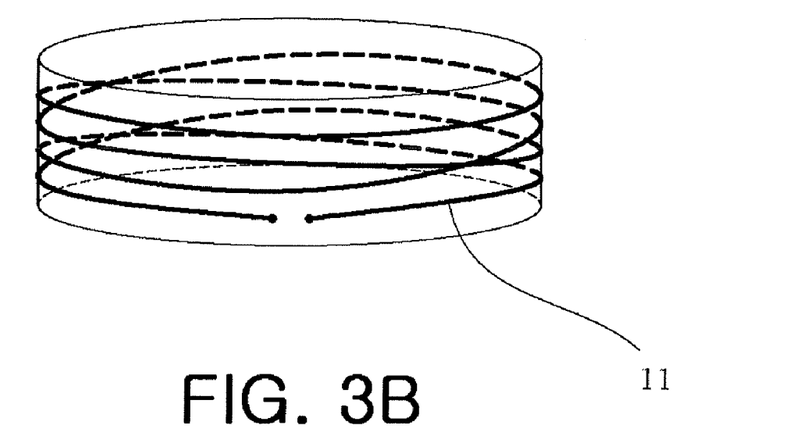
FIG. 3B illustrates another arrangement examples of the electroconductive fiber according to an embodiment of the present invention.

FIG. 2A to FIG. 2C illustrate implementation examples of the electroconductive fiber according to an embodiment of the present invention, and FIG. 3A and FIG. 3B illustrate arrangement examples of the electroconductive fiber according to an embodiment of the present invention.

Referring to FIG. 2A to FIG. 2C, the electroconductive fiber 11 may be implemented in a band type to surround a part of a user's body as illustrated in FIG. 2A, an attachment type that is attachable to a user's clothes as illustrated in FIG. 2B, and a garment type that is woven together with cloth as illustrated in FIG. 2C.

That is, the implementation types of the electroconductive fiber 11 can be variously changed within the scope that can detect changes of the user's body volume or body temperature, while being in contact with the user's skin or being attached to the user's clothing.

In addition, the arrangement types of the electroconductive fiber 11 can be variously changed according to their implementation types. For example, in the case of the band type or the garment type illustrated in FIG. 3B, the electroconductive fiber 11 may be arranged in a spiral shape, and in the case of the attachment type illustrated in FIG. 3A, the electroconductive fiber 11 may be arranged in a zigzag shape.

Such an arrangement of the electroconductive fiber 11 aims at increasing the contact area between the electroconductive fiber 11 and the user's body, thus maximizing changes in the resistance values caused by the user's body volume or body temperature change.

Figure 4:
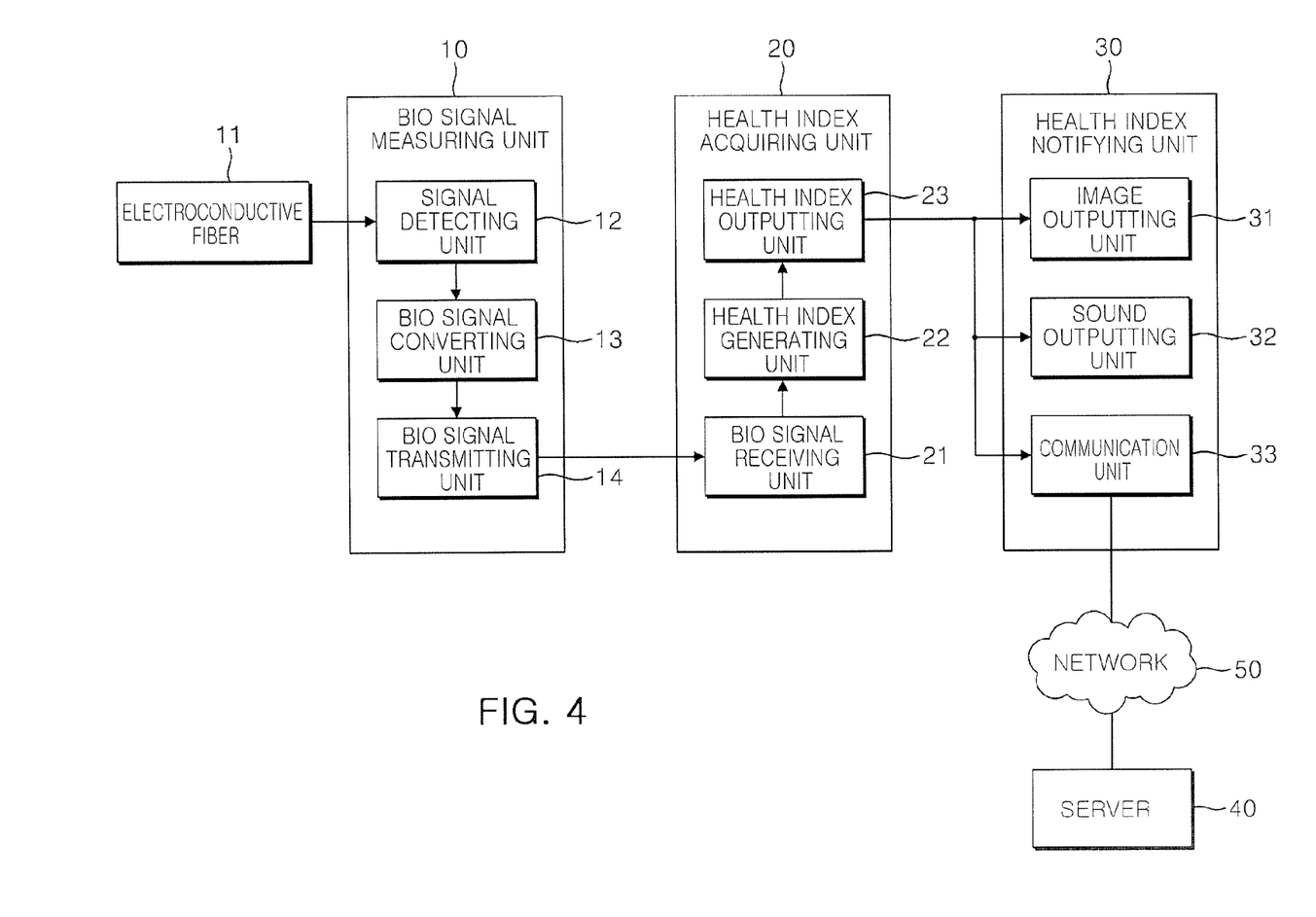
FIG. 4 is a detailed configuration diagram of the apparatus for monitoring a health index using the electroconductive fiber according to an embodiment of the present invention.

FIG. 4 is a detailed block diagram of the apparatus for monitoring the health index using the electroconductive fiber according to an embodiment of the present invention.

Referring to FIG. 4, the bio signal acquiring unit 10 includes a signal detecting unit 12, a bio signal converting unit 13, and a bio signal transmitting unit 14. The signal detecting unit 12 generates an analog signal having a voltage corresponding to a resistance of the electroconductive fiber 11. The bio signal converting unit 13 amplifies and filters the analog signal and converts it into a digital bio signal. The bio signal transmitting unit 14 transmits the digital bio signal to the health index acquiring unit 20.

Figure 5:
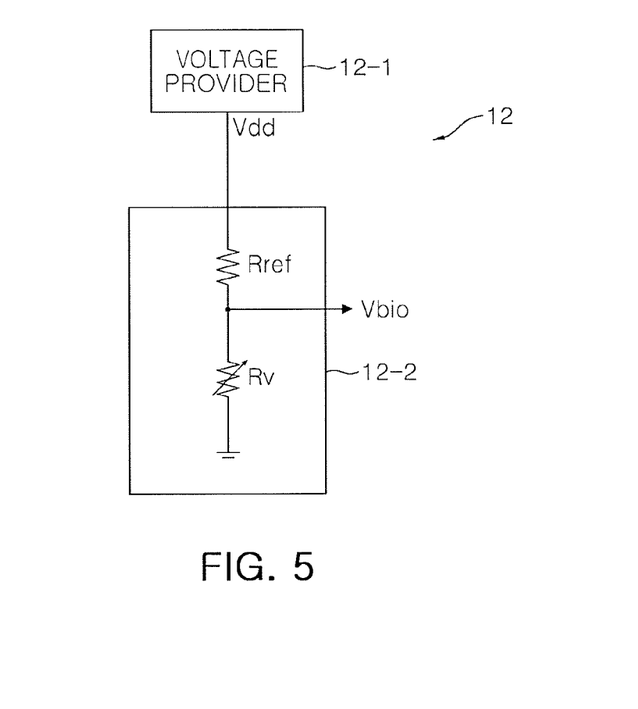
FIG. 5 is a detailed configuration diagram of a bio signal acquiring unit according to an embodiment of the present invention.
Figure 6:
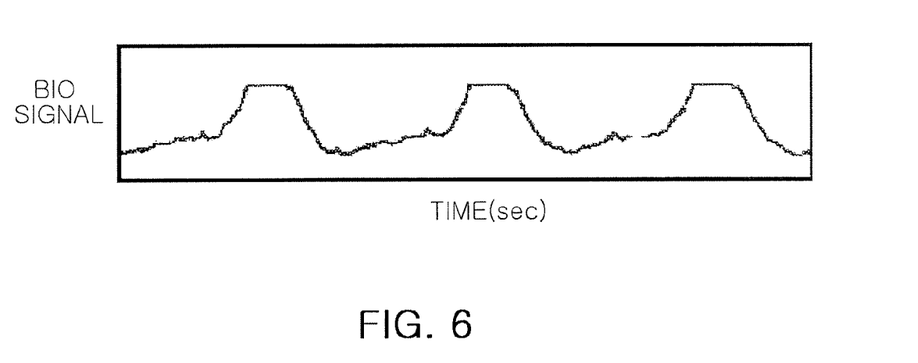
FIG. 6 is a waveform diagram of an analog signal acquired through the bio signal acquiring unit according to an embodiment of the present invention.

The bio signal acquiring unit 10 is implemented with a voltage provider 12-1 generating a certain voltage Vdd, and a voltage division circuit 12-2 recognizing the electroconductive fiber 11 as a variable resistor Rv and dividing the voltage Vdd according to a resistance ratio of the electroconductive fiber 11 to a reference resistance Rref, as illustrated in FIG. 5, and generates the analog signal having a voltage Vbio corresponding to the resistance of the electroconductive fiber 11, as illustrated in FIG. 6.

The health index acquiring unit 20 includes a bio signal receiving unit 21, a health index generating unit 22, and a health index outputting unit 23. The bio signal receiving unit 21 receives the bio signal transmitted from the bio signal acquiring unit 21. The health index generating unit 22 generates a health index by analyzing the received bio signal according to a bio signal analysis standard previously defined by kinds of the health index. The health index outputting unit 23 provides the health index generated from the health index generating unit 22 to the health index notifying unit 30.

At this point, the bio signal analysis standard contains information about change expectation patterns of the bio signal and abnormal detection reference values. And the health index also contains information about the user's current body conditions, occurrences/nonoccurrences of abnormalities, and the types of abnormalities.

The health index notifying unit 30 includes an image outputting unit 31, a sound outputting unit 32, and a communication unit 33. The image outputting unit 31 generates an image corresponding to the health index and outputs it on a screen. The sound outputting unit 32 generates a sound corresponding to the health index and outputs it through a speaker. The communication unit 33 connects to a sever 40 located in the external network through the network 50 and provides the currently acquired health index to the corresponding server 40.

The health index notifying unit 30 provides the current health index to a guardian or doctor positioned at a remote location, as well as the user positioned close to the apparatus for monitoring the health index according to the embodiment of the present invention.

In here, The bio signal acquiring unit 10, the health index acquiring unit 20, and the health index notifying unit 30 perform a communication, based on one of a cable communication, a wireless communication, and an infrared communication, and examples of the wireless communication include wireless technology using short-wave radio frequencies, such as a BLUETOOTH™ communication, a wireless technology using low-power digital radios, such as ZIGBEE™ communication, and a mobile communication.

Figure 7:
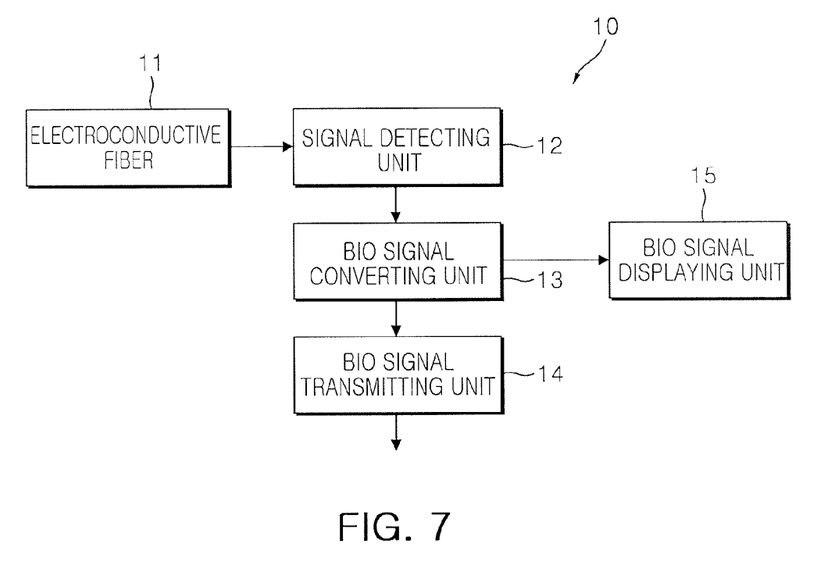
FIG. 7 is a detailed configuration diagram of a bio signal acquiring unit according to another embodiment of the present invention.

Referring to FIG. 7, if necessary, the bio signal acquiring unit 10 may further include a bio signal displaying unit 15 that has a function of displaying the bio signal to immediately notify the currently acquired bio signal to the user.

Figure 8:
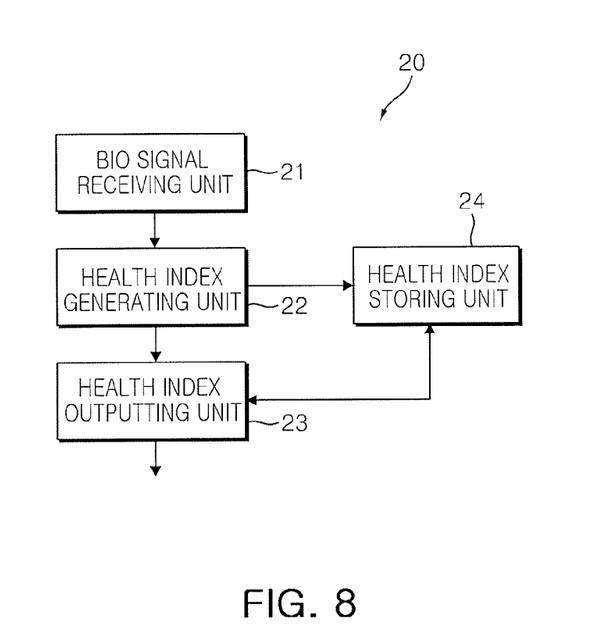
FIG. 8 is a detailed configuration diagram of a health index acquiring unit according to an embodiment of the present invention.

Furthermore, referring to FIG. 8, the health index acquiring unit 20 may further include a health index storing unit 24 that has a memory function of storing the currently acquired health index to enable the user, guardian or doctor to search and monitor a specific health index.

Figure 9:
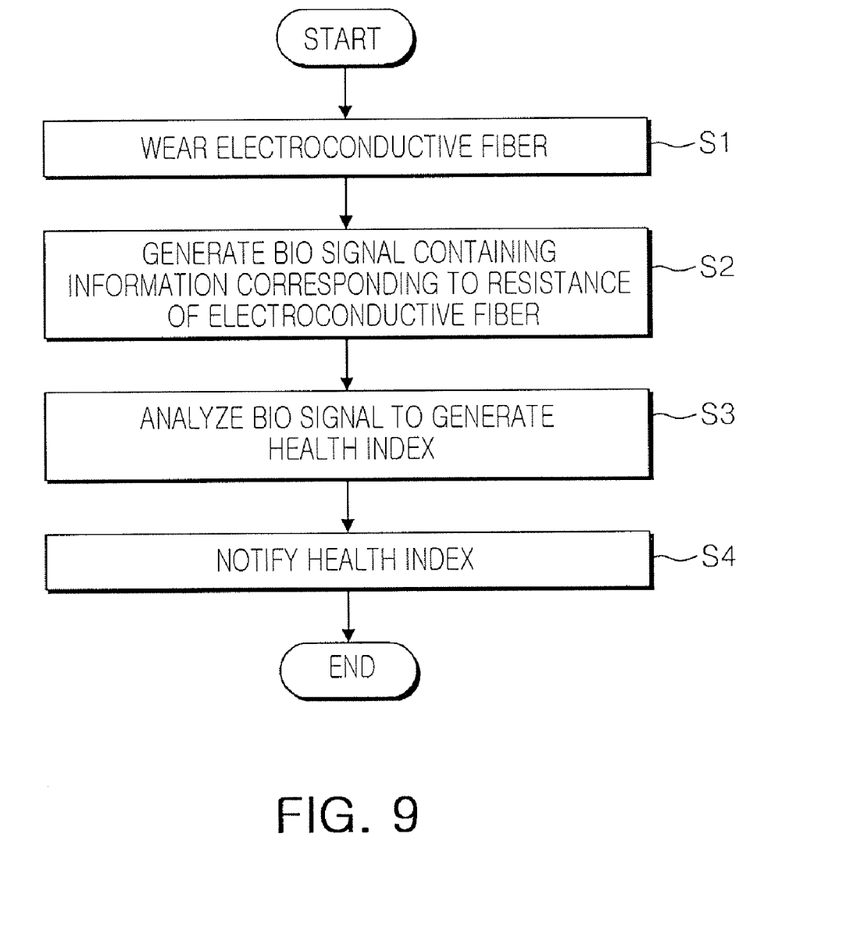
FIG. 9 is a flowchart illustrating a method for monitoring a health index using an electroconductive fiber according to an embodiment of the present invention.

FIG. 9 is a flowchart illustrating a method for monitoring a health index in the apparatus for monitoring the health index using the electroconductive fiber according to an embodiment of the present invention.

For convenience of explanation, a case of acquiring health index related to a user's respiration rate using the electroconductive fiber 11 is exemplified in FIG. 9.

First, when the user wears the electroconductive fiber 11 around his abdomen close to the diaphragm (S1), the resistance of the electroconductive fiber 11 is varied according to the change in the volume of the abdomen when the user breathes, and the bio signal acquiring unit 10 generates a bio signal containing information corresponding to the varied resistance of the electroconductive fiber 11 (S2).

The health index acquiring unit 20 analyzes the bio signal generated in operation S2, based on a bio signal analysis standard associated with the respiration rate, and generates a health index containing information about respiration patterns, respiration normalities/abnormalities, and respiration abnormality types (S3).

The health index notifying unit 30 outputs the health index generated in operation S3 in an image form on a screen and in a sound form through a speaker in the apparatus for monitoring the health index, or provides the health index to a server located at an external network (S4).

Although it has been described above that the bio signal containing one kind of information is acquired through the electroconductive fiber, it is apparent that several electroconductive fibers may be dispersedly disposed in parts of the user's body in an actual application example, and bio signals containing several kinds of information may be simultaneously acquired through the electroconductive fibers.

Moreover, although it has been limited in the above embodiments that only the information about the pulse frequency, the electrocardiogram, the respiration rate and the body temperature is acquired, it is apparent that all bio information generated when the user's body volume or body temperature is changed can be acquired in an actual application example.

In the apparatus and method for monitoring the health index using the electroconductive fiber according to the embodiments of the present invention, the electroconductive fiber may be implemented as the band type, the garment type or the attachment type so that it can be conveniently worn around a part of the user's body, and the user's bio signal may be detected using the characteristic that the resistance of the electroconductive fiber is varied according to the body volume or body temperature change caused by the user's biological activity. Then, the detected bio signals may be analyzed to acquire the health index.

Accordingly, the health index can be easily monitored without limitations on the user's behavior.

While the present application has been shown and described in connection with the exemplary embodiments, it will be apparent to those skilled in the art that modifications and variations can be made without departing from the spirit and scope of the invention as defined by the appended claims.

What is claimed is:

1. An apparatus for monitoring a health index using an electroconductive fiber, the apparatus comprising:
   an electroconductive fiber implemented in a band type to surround a part of a user's body or in a garment type woven together with cloth, wherein the electroconductive fiber is arranged in a spiral shape such that the electroconductive fiber surrounds the part of the user's body more than once;
   a bio signal acquiring unit configured to measure a bio signal using the electroconductive fiber which is worn around the part of the user's body, the electroconductive fiber having a length that varies as the user's body volume or body temperature changes and having an electrical resistance that varies according to the length of the electroconductive fiber;
   a health index analyzing unit configured to analyze the bio signal to determine a health index; and
   a health index notifying unit configured to provide notification of the health index.

2. The apparatus of claim 1, wherein the bio signal contains information about one or more of pulse frequency, electrocardiogram, respiration rate, and body temperature.

3. The apparatus of claim 2, wherein:
   the electroconductive fiber is adapted to be worn around a wrist, and the bio signal acquiring unit acquires a bio signal containing information about the pulse frequency.

4. The apparatus of claim 1, wherein the bio signal acquiring unit comprises:
   a signal detecting unit configured to output an analog signal having a voltage corresponding to the resistance of the electroconductive fiber;
   a bio signal converting unit configured to convert the analog signal into a digital bio signal; and
   a bio signal transmitting unit configured to transmit the digital bio signal to the health index acquiring unit.

5. The apparatus of claim 4, wherein the signal detecting unit comprises:
   a voltage provider generating a voltage necessary for detection of the bio signal; and
   a voltage division circuit configured to divide the voltage according to the resistance of the electroconductive fiber and generating an analog signal having a voltage corresponding to the resistance of the electroconductive fiber.

6. The apparatus of claim 4, wherein the bio signal acquiring unit further comprises a bio signal displaying unit configured to output the bio signal in image and/or sound form.

7. The apparatus of claim 1, wherein the bio signal acquiring unit transmits the bio signal, and the health index acquiring unit comprises:
   a bio signal receiving unit configured to receive the bio signal transmitted from the bio signal acquiring unit;
   a health index generating unit configured to analyze the bio signal to determine the health index; and
   a health index outputting unit configured to output the health index to the health index notifying unit.

8. The apparatus of claim 7, wherein the health index generating unit generates the health index by analyzing the bio signal according to a bio signal analysis standard previously defined by kinds of the health index.

9. The apparatus of claim 1, wherein the health index notifying unit comprises:
   an image outputting unit configured to output an image corresponding to the health index;
   a sound outputting unit configured to output a sound corresponding to the health index; and
   a communication unit configured to connect to a server located in an external network to provide the health index to the server.

10. The apparatus of claim 1, wherein the bio signal acquiring unit, the health index acquiring unit, and the health index notifying unit perform a communication, based on one of a cable communication, a wireless communication, and an infrared communication.

11. A method for monitoring a health index using an electroconductive fiber, the method comprising:
   locating an electroconductive fiber, which has a length that varies as the user's body volume or body temperature changes and has an electrical resistance that varies according to the length of the electroconductive fiber, at a part of a user's body corresponding to the type of bio signal to be measured, the electroconductive fiber being located so as to surround the user's body more than once;
   measuring a bio signal using the electroconductive fiber which is worn around a part of the user's body and of which resistance is varied according to a user's body volume or body temperature;
   analyzing the bio signal to determine a health index; and
   notifying the health index to the user.

12. The method of claim 11, wherein the bio signal contains information about one or more of pulse frequency, electrocardiogram, respiration rate, and body temperature.

13. The apparatus of claim 2, wherein:
   the electroconductive fiber is adapted to be worn around a chest where a heart is located, and the bio signal acquiring unit acquires a bio signal containing information about the electrocardiogram.

14. The apparatus of claim 2, wherein:
   the electroconductive fiber is adapted to be worn around an abdomen between a solar plexus where a diaphragm is located and a navel, and the bio signal acquiring unit acquires a bio signal containing information about the electrocardiogram.

15. The apparatus of claim 2, wherein:
   the electroconductive fiber is adapted to be worn around an abdomen or an armpit that is least affected by an exterior temperature, and the bio signal acquiring unit acquires a bio signal containing information about the body temperature.

16. An apparatus for monitoring a health index using an electroconductive fiber, the apparatus comprising:
   an electroconductive fiber implemented as an attachment type configured to be attached to a user's clothes, wherein the electroconductive fiber is arranged in a spiral shape such that the electroconductive fiber surrounds a part of a user's body more than once;
   a bio signal acquiring unit configured to measure a bio signal using an electroconductive fiber, the electroconductive fiber having a length that varies as the user's body volume or body temperature changes and having an electrical resistance that varies according to the length of the electroconductive fiber;
   a health index acquiring unit configured to analyze the bio signal to determine a health index; and
   a health index notifying unit configured to provide notification of the health index.

17. The apparatus of claim 16, wherein the health index notifying unit comprises:
   an image outputting unit outputting an image corresponding to the health index;

a sound outputting unit outputting a sound corresponding to the health index;

a communication unit connecting to a server located in an external network to provide the health index to the server in order to provide the current health index to a guardian or doctor positioned at a remote location; and a health index storing unit configured to store the currently acquired health index to enable the user, guardian or doctor to search and monitor a specific health index.

18. The apparatus of claim 16, wherein the bio signal acquiring unit comprises:

a signal detecting unit configured to output an analog signal having a voltage corresponding to the resistance of the electroconductive fiber;

a bio signal converting unit configured to convert the analog signal into a digital bio signal; and a bio signal transmitting unit configured to transmit the digital bio signal to the health index acquiring unit.

19. The apparatus of claim 16, wherein the bio signal acquiring unit transmits the bio signal, and the health index acquiring unit comprises:

a bio signal receiving unit configured to receive the bio signal transmitted from the bio signal acquiring unit;

a health index generating unit configured to analyze the bio signal to acquire the health index; and a health index outputting unit configured to output the health index to the health index notifying unit.

* * * * *